United States Patent [19]
Ogata et al.

[11] Patent Number: 5,776,922
[45] Date of Patent: Jul. 7, 1998

[54] CORTICOID DERIVATIVES AND PHARMACEUTICAL AND COSMETIC COMPOSITIONS

[75] Inventors: Kazumi Ogata, Toyonaka; Hideki Tsuruoka, Kawanishi; Takahiro Sakaue; Hidetoshi Nakao, both of Itami, all of Japan

[73] Assignee: Senju Pharmaceutical Co., Ltd., Osaka, Japan

[21] Appl. No.: 688,227

[22] Filed: Jul. 29, 1996

Related U.S. Application Data

[63] Continuation of Ser. No. 365,004, Dec. 28, 1994, abandoned.

[30] Foreign Application Priority Data

Jan. 28, 1994 [JP] Japan .................................. 6-008236

[51] Int. Cl.$^6$ .......................... C07F 9/09; A61K 31/665
[52] U.S. Cl. ........................ 514/172; 540/5; 514/171
[58] Field of Search ................ 540/5; 514/171, 514/172, 99

[56] References Cited

U.S. PATENT DOCUMENTS 4,939,128  7/1990  Kato et al. ............................ 540/5

FOREIGN PATENT DOCUMENTS

A 2 475 048   7/1981   France .
WO 93/03732   4/1993   WIPO .

OTHER PUBLICATIONS

Patent Abstracts of Japan; vol. 016, No. 338 (22 Jul. 1992); JP–A 4 099 772 Kanebo Ltd.; 31 Mar. 1992.
The Merck Index, Eleventh Edition, 1989, pp. 130–131 and 184.

*Primary Examiner*—Mukund J. Shah
*Assistant Examiner*—Pavanaram K. Sripada
*Attorney, Agent, or Firm*—Armstrong, Westerman, Hattori, McLeland & Naughton

[57] ABSTRACT

1. A corticoid derivative of the general formula

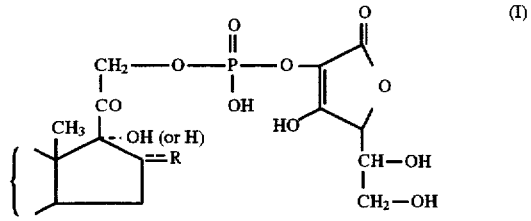

(I)

wherein R represents hydrogen, hydroxy, methyl or methylene; inclusive of the acylation product thereof where the 17-position of the steroid skeleton is hydroxy and the ketone form thereof where R is hydroxy, or a physiologically acceptable salt thereof.

Since the corticosteroid derivative of this invention is readily soluble in water and has antiallergic, antiinflammatory and antioxidant activities, it can be used with advantage in the prevention and therapy of various allergic diseases, inflammatory diseases, cataract and various ischemic organ diseases.

5 Claims, 2 Drawing Sheets

CORTICOID DERIVATIVES AND PHARMACEUTICAL AND COSMETIC COMPOSITIONS

This application is a continuation of application Ser. No. 08/365,004 filed Dec. 28,1994, now abandoned.

FIELD OF THE INVENTION

This invention relates to a novel and useful class of derivatives of various corticosteroids (hereinafter referred to sometimes as corticoids), processes for their production, and useful compositions containing said derivatives as active ingredients. More particularly, this invention relates to 21-(ascorbyl-2-phosphoryl) corticoids, physiologically acceptable salts thereof, processes for producing said derivatives or salts, and pharmaceutical and cosmetic compositions containing them as active ingredients.

BACKGROUND OF THE INVENTION

Corticosteroids or corticoids as secreted from the adrenal cortex are compounds having a steroid skeleton in common and, according to their categories of physiological activity, are roughly classified into mineralocorticoids and glucocorticoids.

Mineralocorticoids are hormones having mineralmetabolizing activity and as such are associated with the metabolism of inorganic salts. Mineralocorticoids modulate the excretion of sodium chloride and water, and being reserved in the interstitium, promote the renal excretion of potassium and phosphate ions, thus being factors vital to animals for the maintenance of life. Among the mineralocorticoids so far known are aldosterone, desoxycorticosterone and corticosterone, to mention but a few typical examples.

On the other hand, glucocorticoids are corticosteroids having carbohydrate-metabolizing activity. Thus, they convert tissue proteins to carbohydrates and increases hepatic glycogen stores to increase the resistance of the body to shock, cold, trauma and poisoning to thereby discharge an antiallergic function. Furthermore, glucocorticoids have antiinflammatory activity. Among the known glucocorticoids are cortisone, hydrocortisone, prednisolone, methylprednisolone, triamcinolone, dexamethasone, paramethasone, clocortolone, fluocinolone, clobetasone and betamethasone.

Having such multiple physiolosical activities, corticoids are in broad use in the treatment of, for example, stress, shock, allergic diseases and inflammatory diseases. However, they have the disadvantage of being only sparingly soluble in water. As watersoluble corticoid derivatives, the corresponding phosphates and metasulfobenzoates are known.

The inventors of this invention did much research to develop new water-soluble substances having both high antioxidant activity and potent adrenocortical hormone activity and succeeded in synthesizing a class of compounds having the structure that ascorbic acid is bound to a corticoid through phosphoric acid, inclusive of their salts. They discovered that these compounds satisfy the above-mentioned requirement and did further research, which has resulted in the development of this invention.

SUMMARY OF THE INVENTION

This invention, therefore, relates to (1) corticoid derivatives of the following formula or physiologically acceptable salts thereof (hereinafter referred to collectively as the present compound), (2) processes for producing the present compound, and (3) useful compositions containing the present compound.

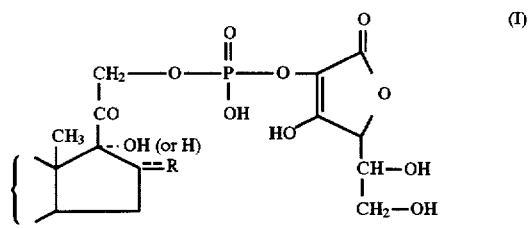

DETAILED DESCRIPTION OF THE INVENTION

Figure 1:
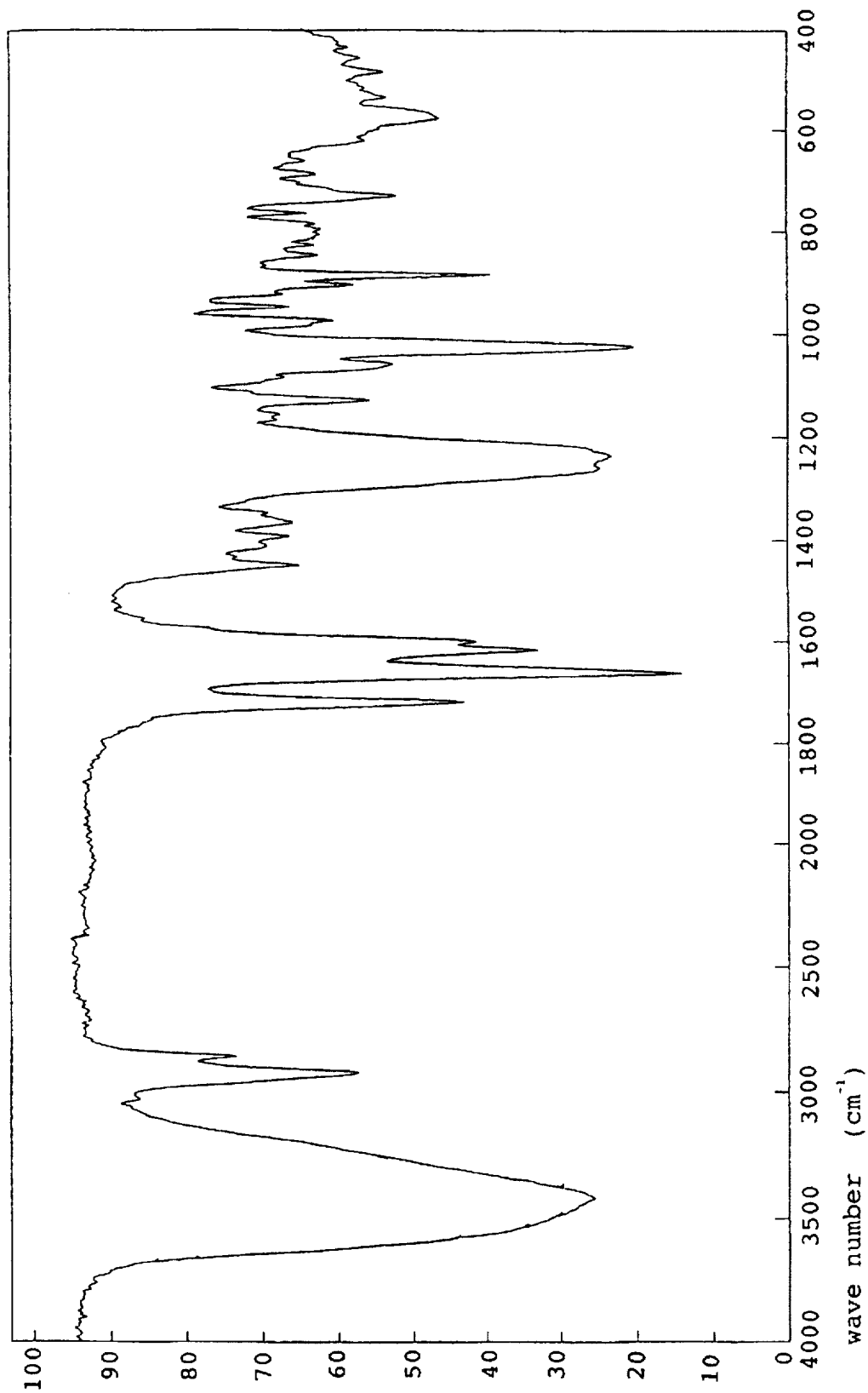

The present compound can be used, regardless of whether it is a free compound or a physiologically acceptable salt, for purposes of this invention. The physiologically acceptable salt typically includes salts with alkali metals such as sodium and potassium and salts with alkaline earth metals such as calcium and magnesium. Aside from them, any other kind of salt can be used that is physiologically or pharmacologically acceptable.

The corticoid that can be used in this invention is any corticosteroid having an alcoholic hydroxyl group or a halogen atom in 21-position of the steroid skeleton. As typical such mineralocorticoids, aldosterone, desoxycorticosterone, corticosterone, etc. can be mentioned. As typical such glucocorticoids, cortisone, hydrocortisone, prednisolone, methylprednisolone, triamcinolone, triamcinolone acetonide, dexamethasone, paramethasone, clocortolone, fluocinolone, clobetasone, betamethasone, etc. can be mentioned.

The present compound can be synthesized by, for example, the following two alternative routes. Thus, one process, as shown by the following reaction schema, comprises reacting a corticoid having an alcoholic hydroxyl group in 21-position of the steroid skeleton (II) with an ascorbyl-2-phosphate (III) in the presence of a dehydrative condensing agent to provide the present compound (I).

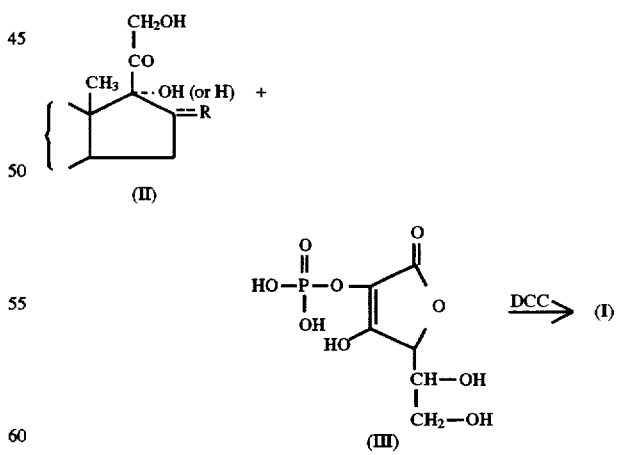

Another process, as shown by the following reaction schema, comprises reacting a corticoid having a halogen atom in 21-position of the steroid skeleton (IV) with an ascorbyl-2-phosphate (III) in the presence of an acid acceptor to provide the present compound (I).

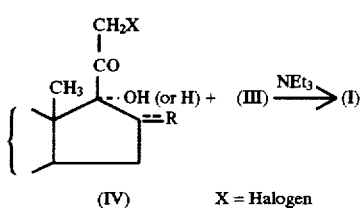

(IV)   X = Halogen

These two processes are now described in further detail.

In the first-mentioned process (I), a corticoid having an alcoholic hydroxyl group in 21-position of the steroid skeleton (II) is condensed with an ascorbyl-2-phosphate (III) in the presence of a dehydrative condensing agent such as pyridine. The ascorbyl-2-phosphate (III) can be synthesized by the known process for the production of a salt of ascorbyl-2-phosphoric acid but a commercial product can be purchased and used. Moreover, the ascorbic acid may be whichever of the L-form or of the DL-form. For use in the present reaction, magnesium ascorbyl-2-phosphate, for instance, is passed through a sulfonic acid-form ion exchange resin to remove the magnesium ion and the resulting free acid is used. While the dehydrative condensing agent that can be used includes many kinds of compounds, typically N,N'-dicyclohexylcarbodiimide (DCC) can be used with advantage. As the reaction solvent, pyridine is a preferred example but any other solvent that does not interfere with the reaction can be employed. This reaction can be carried to completion in about 1–5 hours at ambient temperature.

In the second-mentioned process (II) for the synthesis of the present compound, a corticoid having a halogen atom in 21-position of the steroid skeleton (IV) and ascorbyl-2-phosphate (III) are refluxed in a ketone solvent in the presence of an organic amine for several hours. The corticoid having a halogen atom in 21-position of the steroid skeleton, of the formula (IV), can be prepared by, for example, the following allternative processes. The corticoid having an alcoholic hydroxyl group in 21-position of the steroid skeleton is reacted with p-toluenesulfonyl chloride in dimethylformamide (DMF) to provide the chloro-compound. This chloro-compound can be further treated with sodium iodide in acetone to provide the iodo-compound. While the chloro-compound can be used for the present reaction, the iodo-compound, which is more reactive, can be used more advantageously. The reaction solvent is preferably a ketone, e.g. acetone, methyl ethyl ketone, etc., but any other solvent that does not interfere with the reaction can be employed. The acid acceptor is preferably an organic tertiary amine such as triethylamine or tributylamine. This reaction goes to completion under reflux in about 1–5 hours.

The compound (I) thus synthesized can be converted to a physiologically acceptable salt. The conversion of compound (I) to such a salt can be effected by, for example, adding an alkali metal or alkaline earth metal ion donor, such as the corresponding hydroxide, carbonate or hydrogen carbonate, thereto in an appropriate solvent. This conversion procedure can be carried out after isolation of compound (I) or prior to isolation from the reaction mixture.

The present compound (I) is a novel and very useful compound not heretofore mentioned in the literature and by virtue of its antioxidant, antiinflammatory and antiallergic activities, finds application not only as an antioxidant, antiinflammatory agent, antiallergic agent, etc. in the medical field but also as a cosmetic ingredient in the cosmetic field.

The disease which responds to the antioxidant action of the present compound includes cataract and ischemic organ diseases, among others.

The inflammatory disease in which the pharmaceutical composition of this invention can be indicated includes hemorrhoids, rheumatoid arthritis, degenerative rheumatism, spondylitis deformans, osteoarthritis, lumbago, gouty attack, acute otitis media, cystitis, prostatitis, dentalgia, uveitis, sinuitis and so on.

The allergic disease in which the pharmaceutical composition of this invention can be indicated includes bronchial asthma, pollinosis, allergic rhinitis, alimentary allergic gastritis, allergic diarrhea, ulcerative colitis, stomatitis, periarteritis nodosa, endarteritis obliterans, endocarditis, urticaria, eczema, contact dermatitis, phlyctena, sympathetic ophthalmia, allergic conjunctivitis, allergic keratitis and so on.

In the cosmetic field, the present compound can be incorporated in creams, lotions and other cosmetic formulations as an ultraviolet-absorbing skin care ingredient or as a stabilizer for other cosmetic ingredients, for instance.

The pharmaceutical composition of this invention can be administered, either orally or otherwise, for the prevention and therapy of the above-mentioned diseases. The dosage form in which the pharmaceutical composition of this invention can be supplied includes a variety of solid dosage forms such as tablets, granules, powders, capsules, ointments, suppositories, etc. and liquid dosage forms such as eyedrops, injections, syrups and so on. These dosage forms can be manufactured by the established pharmaceutical procedures. In the manufacture of such dosage forms, the known carriers and additives such as the excipient, binder, disintegrating agent, thickener, dispersant, reabsorption promoter, buffer, surfactant, preservative, isotonizing agent, stabilizer and pH control agent can be employed in appropriate amounts. The cosmetic composition of this invention may contain various other ingredients which are generally incorporated in cosmetic products.

The pharmaceutical and cosmetic compositions of this invention may respectively contain one or more species of the present compound according to the intended use and need.

In medical applications of the present compound, its dosage depends on the species of compound, the type of disease to be prevented or cured, the patient's age, sex and body weight, clinical symptoms to be managed, and treatment modality, but the recommended daily adult dose is about 0.1 mg–30 mg in the case of an injectable preparation. In the case of an oral preparation, about 1 mg–100 mg can be administered a few times a day to the average adult. For ophthalmic use, a preparation of about 0.01–0.5% (w/v) concentration can be instilled into the eye a few drops per dose several times daily.

For cosmetic use, the proper amount of the present compound can be selected according to the species of compound, the kind of cosmetic product to which it is added, the specific purpose of addition, etc. but is generally about 0.001–5% and preferably about 0.01–2%.

Unless contrary to the spirit and object of this invention, the pharmaceutical composition of this invention may further contain other adrenocortical hormones, antioxidants, antiallergic agents, antiinflammatory agents and/or other kinds of medicinal substances.

EXAMPLES

The following examples and test examples are intended to describe this invention in further detail.

Example 1
21-(L-Ascorbyl-2-phosphoryl)dexamethasone sodium

In 30 ml of water is dissolved 3.0 g of magnesium L-ascorbyl-2-phosphate and the solution is passed through an Amberlite IR-120B (H+-form) column (2 cm dia. ×35 cm long). The magnesium-free aqueous solution thus obtained is concentrated under reduced pressure on a water bath not over 40° C. and 40 ml of pyridine is added to the residual oil. Then, 2.0 g of dexamethasone is added and dissolved. While the mixture is stirred at ambient temperature, 3.5 g of N,N'-dicyclohexylcarbodiimide (DCC) is added and the mixture is further stirred for 3 hours. The precipitated byproduct dicyclohexylurea is filtered off and the solvent is distilled off. The residue is dissolved in 70 ml of water and neutralized with 2N-sodium hydroxide and the insoluble matter is filtered off. The filtrate is extracted with ethyl acetate to remove the unreacted dexamethasone and the aqueous solution is concentrated under reduced pressure. The resulting white crystals are collected by filtration and recrystallized from water-ethanol to provide 1.5 g of the title compound melting at 195°–196° C. (decomp.). The IR spectrum of this product is shown in FIG. 1.

TLC (silica gel) Rf=0.71 (n-butanol-acetic acid-water= 4:1:1)

Elemental analysis for $C_{28}H_{35}FO_{13}PNa \cdot H_2O$ Calcd.(%): C, 50.15; H, 5.56 Found (%): C, 50.39; H, 5.88

Example 2
21-(L-Ascorbyl-2-phosphoryl)hydrocortisone magnesium

Figure 2:
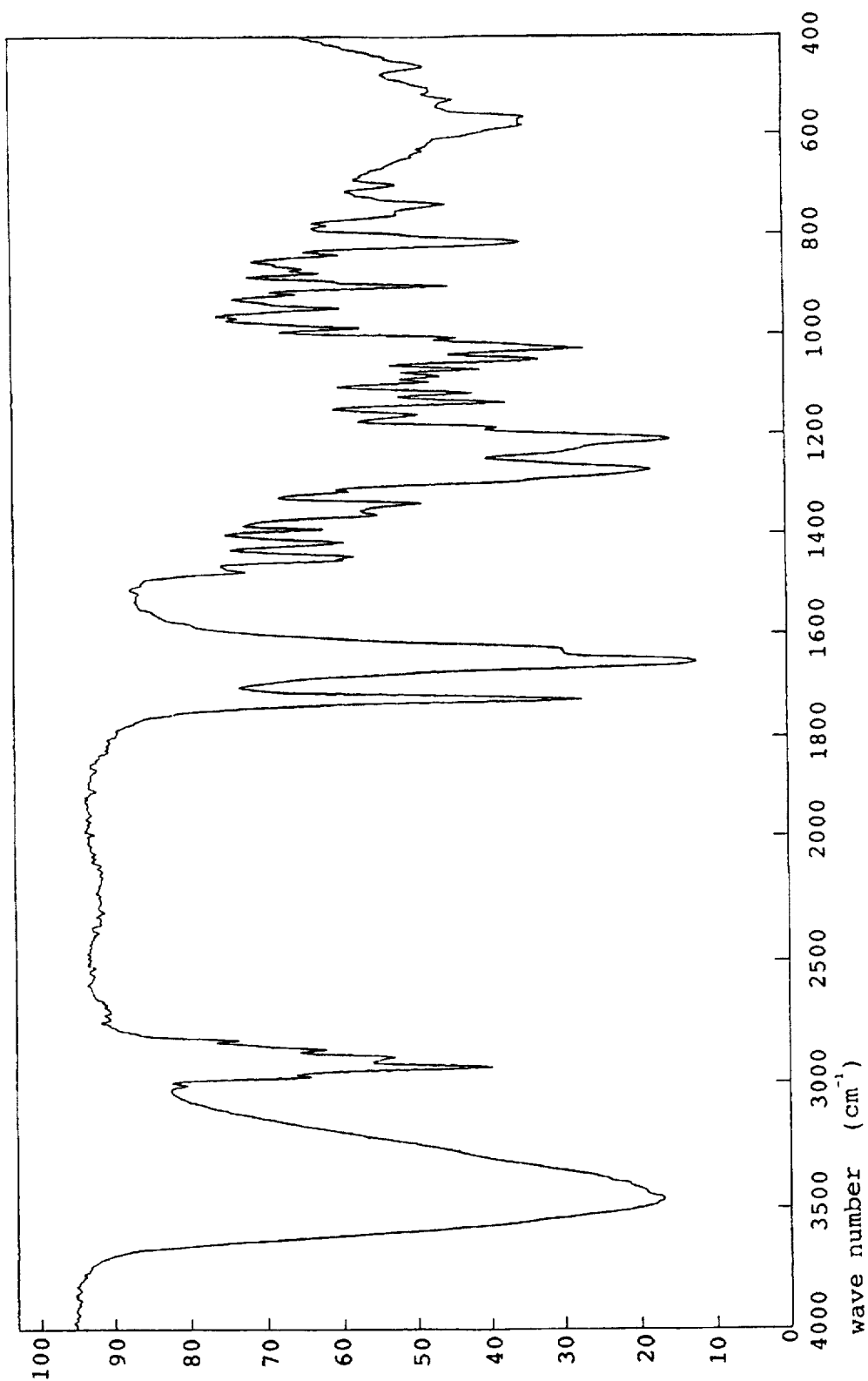

Magnesium L-ascorbyl-2-phosphate, 3.0 g, is treated in the same manner as described in Example 1 and the resulting magnesium-free aqueous solution is concentrated. To the oily residue are added 50 ml of acetone, 2.0 g of 21-iodohydrocortisone and 6 ml of triethylamine and the mixture is refluxed on a water bath for 5 hours. The solvent is then distilled off and the residue is dissolved in 80 ml of 0.2 N-hydrochloric acid with constant stirring. The unreacted steroid is extracted with ethyl acetate. The aqueous layer is concentrated to 40 ml and passed through an Amberlite 1R-120B (H+-form) column (2 cm dia.×35 cm long). The effluent is neutralized with basic magnesium carbonate and concentrated. To the residue is added ethanol and the precipitated magnesium ascorbate is separated by filtration and the solvent is distilled off. The residue is dissolved in 20 ml of water and passed through a Sephadex G-10 column (3 cm dia.×50 cm long, eluent=methanol–water=1:1). The active fractions are pooled and concentrated and the precipitated white crystals are recovered by filtration and recrystallized from a small amount of water to provide 0.91 g of the title compound melting at 164°–165° C. (decomp.). The IR spectrum of this product is shown in FIG. 2.

TLC (silica gel) Rf=0.64 (n-butanol-acetic acid-water= 4:1:1)

Elemental analysis for $C_{54}H_{72}O_{26}P_2Mg \cdot 2H_2O$ Calcd.(%): C, 51.50; H, 6.08 Found (%): C, 51.21; H, 6.45

Example 3
21-(L-Ascorbyl-2-phosphoryl)triamcinolone acetonide sodium

Using 1.5 g of magnesium L-ascorbyl-2-phosphate, 1.0 g of triamcinolone acetonide, 30 ml of pyridine and 2.0 g of DCC, the reaction and treatment described in Example 1 are repeated to provide 0.4 g of the title compound as white crystals melting at 215°–216° C. (decomp.).

TLC (silica gel) Rf=0.71 (n-butanol-acetic acid-water= 4:1:1)

Elemental analysis for $C_{30}H_{37}O_{14}FPNa \cdot H_2O$ Calcd.(%): C, 50.56; H, 5.52 Found (%): C, 50.85; H, 5.87

Example 4
Effect of the present compound on rat carrageenin pleuritis

The effect of the compound of carrageenin-induced pleuritis in rats was evaluated.

[Test substance]
21-(L-Ascorbyl-2-phosphoryl)dexamethasone sodium (abbreviation: Dex-PC)

[Method]

In this test, male 6-week-old S.D. rats (body weights 163–184 g) were used. Under ether anesthesia, 0.1 ml of 2% λ-carrageenin solution was infused into the pleural cavity of the rat to induce pleuritis.

Five hours after administration of λ-carrageenin, Pontamine sky blue (60 mg/2 ml/kg) was injected intravenously and the rat was bled to death 20 minutes later. The chest was opened to collect the pleural exudate and the volume of the exudate and the concentration of the dye in the exudate were determined. The test substance was dissolved in the 2% λ-carrageenin solution at a concentration of 0.1% and administered into the pleural cavity (0.1 mg/site).

[Results]

The results are shown in Table 1.

TABLE 1

Effect of the compound on carrageenin-induced pleuritis in rats

|  | Amount of exudate (ml) | Dye leakage (μg/site) | n |
|---|---|---|---|
| Control | 1.65 ± 0.45 | 68.4 ± 23.3 | 9 |
| Dex-PC | 1.13 ± 0.24* | 43.7 ± 13.2* | 8 |

Each value represents mean ± standard deviation. Significantly different from the control group
*$p < 0.05$.

It is apparent from Table 1 that the compound at a dose of 0.1 mg/site significantly suppressed the amounts of pleural exudate and dye leakage by 31.5% and 36.1%, respectively. These results indicate that the present compound is useful as an antiinflammatory agent.

Formulation Example 1
Oral Tablet

Compound of Example 2 50 mg
Lactose 80 mg
Starch 17 mg
Magnesium stearate 3 mg

Using the above ingredients per tablet, tablets are manufactured by the routine procedure. The tablets may be sugar-coated.

Formulation Example 2
Ophthalmic solution

Compound of Example 1 100 mg
Boric acid 700 mg
Borax 400 mg
Sodium chloride 500 mg
Methyl p-hydroxybenzoate 26 mg
Butyl p-hydroxybenzoate 14 mg
Sterile purified water to make 100 ml The above ingredients are mixed in the routine manner to provide an ophthalmic solution.

Formulation Example 3
Injection

Compound of Example 1 10 mg

Sodium chloride 900 mg

Distilled water to make 100 ml

The above ingredients are mixed in the routine manner to provide an injection.

Formulation Example 4

Ointment

Compound of Example 3 100 mg

Hydrophilic ointment base to make 100 g

The above ingredients are mixed in the routine manner to provide an ointment.

Since the corticosteroid derivative of this invention is readily soluble in water and has antiallergic, antiinflammatory and antioxidant activities, it can be used with advantage in the prevention and therapy of various allergic diseases, inflammatory diseases, cataract and various ischemic organ diseases. Furthermore, the present compound is of value as an ultraviolet absorber, a skin care ingredient, or a stabilizer for other cosmetic ingredients in the field of cosmetics.

What is claimed is:

1. A corticoid derivative selected from the group consisting of 21-(L-ascorbyl-2-phosphoryl) dexamethasone, 21-(L-ascorbyl-2-phosphoryl)hydrocortisone, 21 -(L-ascorbyl-2-phosphoryl) triamcinolone acetonide and physiologically acceptable salts thereof.

2. An antiinflammatory composition comprising a therapeutically effective amount of 21-(L-ascorbyl-2-phosphoryl) dexamethasone or a physiologically acceptable salt thereof.

3. A method of treating inflammatory diseases, allergic diseases, cataract or ischemic organ diseases comprising administering to a patient in need of such treatment a therapeutically effective amount of a corticoid derivative of the formula (I):

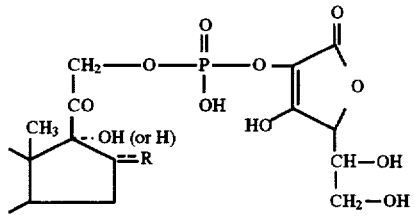

wherein R represents, hydrogenm, hydroxy, methyl or methylene, and wherein the steroid skeleton is a corticosteroid having an alcoholic hydroxyl group or halogen in the 21 position and is selected from the group consisting of aldosterone, desoxycorticosterone, corticosterone, cortisone, hydrocortisone, prednisolone, methylprednisolone, triamcinolone, triamcinolone acetonide, dexamethasone, paramethasone, clocortolone, fluocinolone, clobetasone and betamethasone, and physiologically acceptable salts thereof.

4. A method of treating an inflammatory disease comprising the step of administering a composition comprising an effective amount of 21-(L-ascorbyl-2-phosphoryl) dexamethasone or physiologically acceptable salt thereof to a patient.

5. A cosmetic composition comprising a corticoid derivative selected from the group consisting of 21-(L-ascorbyl-2-phosphoryl)dexamethasone, 21-(L-ascorbyl-2-phosphoryl) hydrocortisone, 21-(L-ascorbyl-2-phosphoryl) triamcinolone acetonide and physiologically acceptable salts thereof.

* * * * *